(12) United States Patent
Vogele

(10) Patent No.: US 12,734,013 B2
(45) Date of Patent: Sep. 15, 2026

(54) MOTORIZED POSITIONING ARM

(71) Applicant: ISYS MEDIZINTECHNIK GMBH, Kitzbühel (AT)

(72) Inventor: Michael Vogele, Schwabmünchen (DE)

(73) Assignee: Isys Medizintechnik GmbH, Kitzbühel (AT)

( * ) Notice: Subject to any disclaimer, the term of this patent is extended or adjusted under 35 U.S.C. 154(b) by 675 days.

(21) Appl. No.: 18/021,704

(22) PCT Filed: Jun. 22, 2021

(86) PCT No.: PCT/EP2021/067028
§ 371 (c)(1),
(2) Date: Feb. 16, 2023

(87) PCT Pub. No.: WO2022/042898
PCT Pub. Date: Mar. 3, 2022

(65) Prior Publication Data

US 2023/0372055 A1 Nov. 23, 2023

(30) Foreign Application Priority Data

Aug. 26, 2020 (DE) ..................... 10 2020 122 352.8

(51) Int. Cl.
*A61B 90/50* (2016.01)
*A61B 90/00* (2016.01)

(52) U.S. Cl.
CPC ........ *A61B 90/50* (2016.02); *A61B 2090/034* (2016.02); *A61B 2090/508* (2016.02)

(58) Field of Classification Search
CPC .............. A61B 34/30; A61B 2034/301; A61B 2034/302; A61B 2034/303;
(Continued)

(56) References Cited

U.S. PATENT DOCUMENTS

2005/0165271 A1 7/2005 Shioda et al.
2008/0150754 A1 6/2008 Quendt
(Continued)

FOREIGN PATENT DOCUMENTS

DE 602004003318 T2 3/2007
DE 102014016824 A1 5/2016
(Continued)

OTHER PUBLICATIONS

English Language Machine Translation of WO2017/144172 A1.
(Continued)

*Primary Examiner* — Tan-Uyen T Ho
*Assistant Examiner* — Bridget E. Rabaglia
(74) *Attorney, Agent, or Firm* — Lerner David LLP

(57) ABSTRACT

A motorized positioning arm is disclosed for positioning instruments, in particular medical instruments, wherein the motorized positioning arm includes at least two arm elements connected to one another so as to be pivotable about a pivot axis by means of a central joint. At least one of the arm elements includes a further joint at an end opposite to the central joint. The motorized positioning arm includes a blocking mechanism for blocking and releasing the central joint and the at least one further joint. The blocking mechanism includes a central shaft arranged coaxially with the pivot axis, and at least one transmission device from the central shaft to the at least one further joint. The blocking mechanism includes an electrical blocking device configured to engage with the central shaft to enable blocking and unblocking of the joints. The electrical blocking device is configured to move along the central shaft.

15 Claims, 4 Drawing Sheets

(58) Field of Classification Search
CPC ........ A61B 2034/304; A61B 2034/305; A61B 2034/306; A61B 34/35; A61B 34/37; A61B 34/70; A61B 34/72; A61B 34/73; A61B 34/20; B25J 9/1689; B25J 15/04; B25J 15/0019; B25J 15/02; B25J 9/0084; B25J 9/1682; B25J 9/0087; B25J 9/04; B25J 9/108; B25J 9/02; B25J 19/0041; B25J 18/04; B25J 15/0052; B25J 18/00; B25J 15/026; B25J 19/0004; B25J 17/02; B25J 7/00; B25J 9/042
See application file for complete search history.

(56) References Cited

U.S. PATENT DOCUMENTS

| | | | | |
|---|---|---|---|---|
| 2017/0065365 | A1* | 3/2017 | Schuh | A61B 90/50 |
| 2017/0258536 | A1* | 9/2017 | Yeung | A61B 34/76 |
| 2018/0055584 | A1* | 3/2018 | Farritor | B25J 9/0024 |
| 2018/0116758 | A1 | 5/2018 | Schlosser et al. | |
| 2018/0132899 | A1* | 5/2018 | SooHoo | A61B 34/70 |
| 2018/0264655 | A1 | 9/2018 | Kuroda et al. | |

FOREIGN PATENT DOCUMENTS

| | | | |
|---|---|---|---|
| EP | 2379284 | B1 | 2/2018 |
| GB | 2515476 | A | 12/2014 |
| JP | 2005204999 | A | 8/2005 |
| JP | 2008142550 | A | 6/2008 |
| JP | 2018509273 | A | 4/2018 |
| KR | 20190140787 | A | 12/2019 |
| WO | 2014203005 | A1 | 12/2014 |
| WO | WO2016/160272 | A1 | 10/2016 |
| WO | WO2017/144172 | A1 | 8/2017 |

OTHER PUBLICATIONS

European Patent Office, Examination Report, Notice under Article 94(3) EPC, for EP21739272.9-1113, dated Mar. 10, 2023.
German patent Office, Examination Report, for DE102020122352.8, dated Apr. 27, 2021.
English Language Machine Translation of DE602004003318.
European Patent Office, International Search Report for PCT/EP2021/067028, dated Oct. 11, 2021.

* cited by examiner

MOTORIZED POSITIONING ARM

CROSS REFERENCE TO RELATED APPLICATIONS

This application is a US national stage filing of international patent application PCT/EP20217067028, filed Jun. 22, 2021 which claims the benefit of priority to German patent application 102020122352.8, filed on Aug. 26, 2020, the content of both of which is herein incorporated by reference.

BACKGROUND OF THE INVENTION

Field of the Invention

The present invention relates to a motorized positioning arm for positioning instruments, in particular medical instruments.

Description of Related Art

A wide variety of positioning arms with different requirements are known from the state of the art for different applications. Particularly in the case of positioning arms for positioning medical instruments, for example, very high demands are placed on the stability, reliability and operability of the positioning arms. Thus, numerous attempts have been made in the prior art to develop and improve positioning systems taking these requirements into account.

For example, a positioning arm with a rotating body or swivel joint and two arm elements pivoted hereto is known from the publication WO 2017/144 172 A1. There, the angle between the two arm elements can be locked by a ratchet attached to the rotating body via a coupling, wherein a switch is provided on the coupling, which locks the angular position of the arms relative to each other in a switch position.

The positioning arm known from the publication WO 2017/144 172 A1 has the advantage that by means of the ratchet it is possible to lock, i.e., block, the rotary joint of the positioning arm simply and with relatively little force. In particular, the ratchet can be easily operated even in a sterile environment, for example under a sterile cover sheet. In addition, a certain minimum torque can be set by means of the ratchet, so that the blocking of the positioning arm can be performed reliably.

However, the positioning arm known from WO 2017/144 172 A1 still has the disadvantage that operation is always user dependent. Thus, there remains a residual risk in use if the user does not operate the ratchet correctly and the arm gets displaced during a surgical procedure. In addition, the ergonomics or usability is still not optimal. For example, when positioning the positioning arm, the user must simultaneously hold the instrument at the end of the positioning arm and keep an eye on the surgical field. Such a simultaneous procedure is very difficult for the user, especially since relatively high forces must be applied when locking the arm and the rotational movement when turning the ratchet can be in opposing directions with movements of the other hand. In addition, since the positioning arm must be repositioned frequently before, during, and after the procedure, i.e., multiple opening and locking is required, a faster operating option would be desirable. In addition, when using a sterile drape, the ratchet must be moved through the drape under the sterile drape, which is both inconvenient and can lead to wear or failure of the drape.

Based on the aforementioned prior art, it is an object of the present invention to provide a positioning arm which overcomes the problems and disadvantages of the systems known from the prior art and has corresponding advantages over them. In particular, it is the object of the present invention to provide a positioning arm which permits ergonomic, comfortable, fast and largely user-independent operation of the positioning arm even through a sterile drape.

BRIEF SUMMARY OF THE INVENTION

This object is solved by the subject-matter of independent claim 1. Further possible embodiments of the invention are specified in particular in the dependent claims.

The solution according to the invention is to provide a motorized positioning arm for positioning instruments, in particular medical instruments, wherein the motorized positioning arm comprises at least two arm elements which are pivotally connected to each other about a pivot axis by means of a central joint, wherein at least one of the arm elements comprises a further joint at an end opposite to the central joint, wherein the motorized positioning arm comprises a blocking mechanism for blocking and releasing the central joint and the at least one further joint, wherein the blocking mechanism comprises a central shaft arranged coaxially with the pivot axis and at least one transmission device from the central shaft to the at least one further joint, wherein the blocking mechanism comprises an electrical blocking device configured to engage the central shaft to enable blocking and releasing of the joints, and preferably wherein the electrical blocking device is configured to move along the central shaft.

In particular, the motorized positioning arm is used to reliably, i.e., safely and precisely position or hold medical instruments during a procedure on a patient. In particular, such reliable positioning of instruments, for example surgical hooks, endoscopes or needles, is essential during surgical or bioptic procedures. The motorized positioning arm allows motorized locking of the joints. The movements or positioning of the positioning arm itself can be performed completely manually.

When using the motorized positioning arm for positioning medical instruments, for example, one of the arm elements can be configured to be connected via a further joint with a fastening device for an operating table. The other arm element can be configured accordingly connected via a further joint with an instrument holder. The instrument holder is preferably configured as a clamp connection. In this way, a medical technology instrument can be clamped into the instrument holder from the outside without damaging a sterile drape which envelops the motorized positioning arm.

The central shaft, which is configured to be coaxial with the pivot axis of the two arm elements, may comprise a thread. For example, the central shaft may be a clamping bolt.

For example, the transmission device may comprise at least one clamping sleeve arranged on the central shaft. The clamping sleeve may be configured as a threaded sleeve that engages the threads of the central shaft or may be axially slidably arranged on the central shaft.

The transmission device can further comprise a push rod which runs axially inside the arm element and is in operative connection with the clamping sleeve in such a way that the transmission device can lock, i.e., block, the further joint at the end of the arm element. For this purpose, the clamping sleeve can comprise, for example, an inclined running surface against which a transmission body, for example a ball, rests. Alternatively, the clamping sleeve may comprise, for example, a joint socket in which a cam is inserted that is arranged on the transmission body. All in all, the transmission device can be used to transmit an axial movement of the central shaft to an axial movement of the push rod. Thereby, the axial movement of the push rod leads to a blocking of the corresponding joint at the end of the arm element.

Although blocking by means of the blocking device is primarily electrical, manual blocking or release of the joints can also be possible. Thus, the blocking device can also be operated without electrical power. The electrical energy required to operate the blocking device is preferably supplied by means of an accumulator. This eliminates the need for wiring, which can be a source of danger within the operating room.

The object is satisfactorily solved with the motorized positioning arm according to the invention. As a motorized drive unit or actuator, the electric blocking device is very convenient and easy to operate, especially through a sterile drape. When a motorized drive unit is used, no elements, such as the ratchet, need to be moved under the sterile drape. In addition to simplifying operation, this also reduces wear on the sterile drape. Furthermore, the operation is configured to be at least substantially user-independent. In contrast to a manual blocking device, the blocking mechanism cannot be adjusted too weakly here, so that the motorized positioning arm is always stable enough and cannot become displaced during operation. Furthermore, the motorized blocking device allows very fast operation. Complete blocking of the joints of the motorized positioning arm can be provided within a few seconds.

Another advantage of the electric i.e. electrically operated blocking device is its compactness. There have been enormous technical developments in electric drives in recent years. Alternative pressure systems (using compressed air, oil, etc.) are too cost-intensive to manufacture, complex to use and maintain, and pose an avoidable risk to the sterile operating field and the user due to the fluids used. With regard to sterility in particular, it is advantageous that electric drives, i.e., motors including the associated electronics, are now also available in a sterilisable form, especially autoclavable. This is particularly relevant in applications where it is not possible to work with a sterile drape.

Another advantage of the motorized positioning arm is that the blocking device is applied to the central shaft. This enables progressive locking of the joints. Since the blocking device can engage centrally and from the outside via the central shaft in the mechanical blocking mechanism of the motorized positioning arm, the transmission devices, for example push rods, can be moved simultaneously or progressively inside the arm elements with high tensile and compressive forces. This progressive movement then makes it possible to progressively lock and open the entire motorized positioning arm or the individual joints of the arm. In particular, the progressive opening of the individual joints may be desirable to prevent there being only one fully open state in which the motorized positioning arm moves back and forth in an unstable manner.

If the electric blocking device is configured to move relative to, in particular along, the central shaft, the electric blocking device is configured as a movable clamping unit. In particular, the electric blocking device is then also configured to move relative to other parts of the positioning arm, for example relative to the arm element on which the electrical blocking device is arranged.

For moving the electrical blocking device, the central shaft can comprise, for example, an external thread that can be brought into contact with a component of the electrical blocking device that comprises an internal thread. When the component comprising the internal thread is rotated, the component moves up or down the central shaft in threaded engagement. The component may be, for example, an output gear of the electrical blocking device. In particular, the component is connected to the rest of the blocking device such that the rest of the blocking device moves axially along the central shaft together with the component. For this purpose, the component may be arranged on a base body of the blocking device, for example. In particular, the component may be arranged on the base body by means of a bearing, for example a dry bearing. The component can then rotate relative to the base body, but takes the base body with it in the axial direction. The base body may, for example, be an angled piece.

In a preferred embodiment of the present invention, both arm elements each comprise one of the further joints at the end opposite the central joint, wherein the blocking mechanism comprises one transmission device each to the further joint.

In this respect, both transmission devices may be configured as already described. For example, one clamping sleeve can also be configured to be axially displaceable on the central shaft and another clamping sleeve can be configured in threaded engagement with the central shaft. Furthermore, a tandem solution is also conceivable, in which one clamping sleeve is moved along by the other. For example, the central joint can be blocked by friction surfaces of the two clamping sleeves pressing against each other. However, the detailed configuration is of secondary importance here.

An advantageous embodiment provides that the further joint is configured as a ball joint.

A ball joint is a joint with a freely rotatable and pivotable ball. The transmission devices can comprise here, for example, sleeves accommodated in the arm elements, which press against the ball joint by means of the respective push rod and thus enable the joints to be firmly clamped.

According to an advantageous further development of the invention, the electric blocking device comprises an electric motor with an output shaft, wherein the output shaft is oriented perpendicular to the central shaft.

With such a configuration, the advantage lies in a particularly high degree of compactness. In a space saving manner, the electric blocking device can be arranged on one of the arm elements or integrated into them. Usually, only very delimited space is available in most applications, and the best possible access by the operator to the operating field is highly relevant. Motorized positioning arms that extend too far laterally often cannot be operated well enough in the surgical field.

Nevertheless, as an alternative to the perpendicular arrangement, a direct drive in the axial direction of the central shaft would of course also be conceivable. Such a design would have the advantage that the constructive implementation of the attachment of the electrical blocking device is technically easy to implement.

A particularly advantageous embodiment of the present invention provides that the electric blocking device comprises a bevel gearing with an input gear connected to the output shaft of the electric motor and an output gear meshing with the central shaft.

An advantage here is also the particular compactness of the bevel gearing. Further, a high and ratio-independent transmission efficiency can be provided by means of the bevel gearing.

According to an advantageous further development of this embodiment, the output gear is supported by means of at least substantially annular dry bearings.

The use of dry bearings is advantageous here, since liquids are always considered a risk factor in the medical field, even if the relevant parts are all in their entirety inside and encapsulated in the housing. Preferably, the dry bearings are configured from slide promotion plastic. This allows dry bearing at a low and defined resistance. Alternatively, however, the use of ball and needle bearings would also be conceivable, wherein these are then preferably used without lubricant.

According to an advantageous embodiment of the invention, the output gear comprises an internal thread and the central shaft comprises an external thread matching the internal thread.

This makes it easy to transmit power from the electrical blocking device to the central shaft.

In a particularly preferred embodiment, the electrical blocking device is arranged on one of the two arm elements and the output shaft of the electric motor extends at least substantially parallel to the axial direction of the arm element on which the electrical blocking device is arranged.

This represents a particularly space-saving and compact design, so that the advantages already discussed in this respect can be provided. For example, the entire electrical blocking device can be configured to be smaller than 70 mm×150 mm×50 mm.

According to an advantageous further development of this embodiment, the electrical blocking device is detachably attached on the arm element on which the electrical blocking device is configured.

Due to the detachable design, the electrical blocking device can be retrofitted. Thus, the electrical blocking device can be attached to an existing non-motorized positioning arm. In this way, it is possible to improve a manual blocking device, such as the system described at the beginning.

Alternatively, the electrical blocking device can be integrated into the arm element on which the electrical blocking device is arranged. In this case, integrated means that the arm element and the electrical blocking device comprise a housing that is common at least in certain areas.

An advantageous embodiment of the motorized positioning arm further provides that the electric blocking device is configured as a movable clamping unit that is configured to be movable in the axial direction of the central shaft relative to the arm element on which the electric blocking device is arranged.

The electrical blocking device is thus configured as a floating bearing arrangement. In the case of a fixed arrangement mounted on the arm element, the gears either move closer to or further away from each other depending on the degree of opening of the motorized positioning arm. This results in major disadvantages, particularly with regard to wear of the moving, rigid parts. Wear is a critical problem, especially in medical applications. All systems must provide safety over their entire service life. In addition, wear results in only inaccurate force measurement being possible in the electrical blocking device, for example via motor currents, force sensors or distance sensors. However, this inaccurate force measurement is not sufficient to ensure that the motorized positioning arm can be opened and locked safely and user-independently via the electric blocking device.

As a movable clamping unit, the electric blocking device is preferably guided exclusively by means of the central shaft. However, further lateral guidance would be possible by means of a housing. This housing can also prevent the electrical blocking device from rotating during blocking and releasing.

According to a further embodiment of the present invention, the motorized positioning arm comprises a housing by which the electrical blocking device can be at least substantially enclosed, wherein the housing is configured in the shape of a handle.

A housing that encloses, for example, portions of the arm element and the electrical blocking device is advantageous to protect the user and the patient and to ensure adequate cleanability and sterilizability.

Since the housing is configured to be handle-shaped, the housing can also be used as a handle to hold and manually move the corresponding arm element. In this case, the housing is ergonomically designed such that the entire system can be operated with gloves and, if necessary, through a sterile drape. For better grip, the housing can be coated with anti-slip material, at least in some areas.

The housing can be configured as a separate housing of the electrical blocking device. The housing may also be configured integrally with the corresponding arm element, at least in some areas. Especially when the housing is configured integrally with the arm element, the housing may be made of light metal, for example aluminium.

The housing may comprise a cover to allow easy access to the electrical blocking device. This cover may be made of plastic, for example. The housing as a whole preferably meets a protection of IP44 according to DIN EN 60529 (VDE 0470-1):2014-09.

An advantageous embodiment of the motorized positioning arm provides that the electrical blocking device comprises a stop which comes into abutment with the housing and thereby prevents the electrical blocking device from rotating with the housing when the joints are blocked and released.

By means of the housing, a further function is thus fulfilled. In a possible alternative embodiment, the housing of the electrical blocking device can provide even more precise guidance. For example, a linear guide may be configured in the direction of the central shaft.

According to an advantageous further embodiment of the invention, redundant operating elements for controlling the electric motor are arranged on the housing.

The operating elements can, for example, each be a pushbutton or button that is actuated by pressing and can return to the initial position, preferably automatically, after being released. The operating elements are configured in such a way that their positions can be reliably determined by tactile perception. Preferably, the operating elements are arranged in a pocket. This makes it easier to find the buttons and prevents them from being pressed unintentionally. Overall, the entire system can thus be operated advantageously with gloves and, if necessary, through sterile drapes.

The operating elements are configured redundantly to prevent unintentional activation of the blocking device. For example, there are four operating elements, two operating elements configured for blocking and two operating elements configured for releasing the joints. The operating elements are arranged in such a way that the user can hold the handle-like housing, i.e. the corresponding arm element that is also a large part of the weight of the motorized positioning arm, and press the operating elements at the same time.

In addition to the operating elements, other devices can also be configured redundantly. For example, pressure sensors, position sensors, displacement sensors and/or motor current sensors can be configured redundantly. These can provide accurate control of the force applied to the output gear or accurate determination of the state of the blocking device. The cabling is also configured redundantly, for example.

It is advantageous to combine different types of sensors to gain additional safety. Further, more than two sensor systems can be used to gain additional redundancy.

In a particularly preferred embodiment, a charging coil is arranged within the housing for wireless charging of an accumulator suitable for driving the electric motor.

The design for wireless charging eliminates the risk posed by cables in the operating room. Furthermore, the housing can be configured to be particularly well sealed, since there is no need to provide access for a cable. The accumulator can be charged by means of a charging piece. This charging piece can be arranged on the housing. For example, the charging piece and the housing can comprise a complementary geometry such that a mechanical key-lock principle is provided. In this way, reliable charging of the accumulator can be ensured.

According to an advantageous embodiment of the invention, at least one indicator element is arranged on the housing, by means of which a charging state of the accumulator and/or a blocking state of the blocking mechanism can be indicated.

The indicator element can thus indicate a blocking state (for example, fully blocked, fully released, partially blocked, semi-soft) of the motorized positioning arm or of the blocking device by means of sound, vibration and/or visual indication. Preferably, a visual indication is provided, for example, by means of an LED. Alternatively or additionally, the state of charge, i.e. the remaining charge, and/or the charging mode (for example active) of the accumulator can also be indicated. Advantageously, the presence of a low charge is indicated at the latest at a remaining charge that still allows 10 blocking operations.

All of the advantages described above can be used particularly well in a motorized positioning arm for positioning medical instruments.

BRIEF DESCRIPTION OF THE SEVERAL VIEWS OF THE DRAWINGS

Further advantages features and details of the various embodiments of this disclosure will become apparent from the ensuing description of a preferred exemplary embodiment and with the aid of the drawings. The features and combinations of features recited below in the description, as well as the features and feature combination shown after that in the drawing description or in the drawings alone, may be used not only in the particular combination recited, but also in other combinations on their own, with departing from the scope of the disclosure.

Further features, advantages and embodiments of the invention will be disclosed in the following description based on the figures, wherein.

DETAILED DESCRIPTION OF THE INVENTION

As used throughout the present disclosure, unless specifically stated otherwise, the term "or" encompasses all possible combinations, except where infeasible. For example, the expression "A or B" shall mean A alone, B alone, or A and B together. If it is stated that a component includes "A, B, or C", then, unless specifically stated otherwise or infeasible, the component may include A, or B, or C, or A and B, or A and C, or B and C, or A and B and C. Expressions such as "at least one of" do not necessarily modify an entirety of the following list and do not necessarily modify each member of the list, such that "at least one of "A, B, and C" should be understood as including only one of A, only one of B, only one of C, or any combination of A, B, and C.

Figure 1:
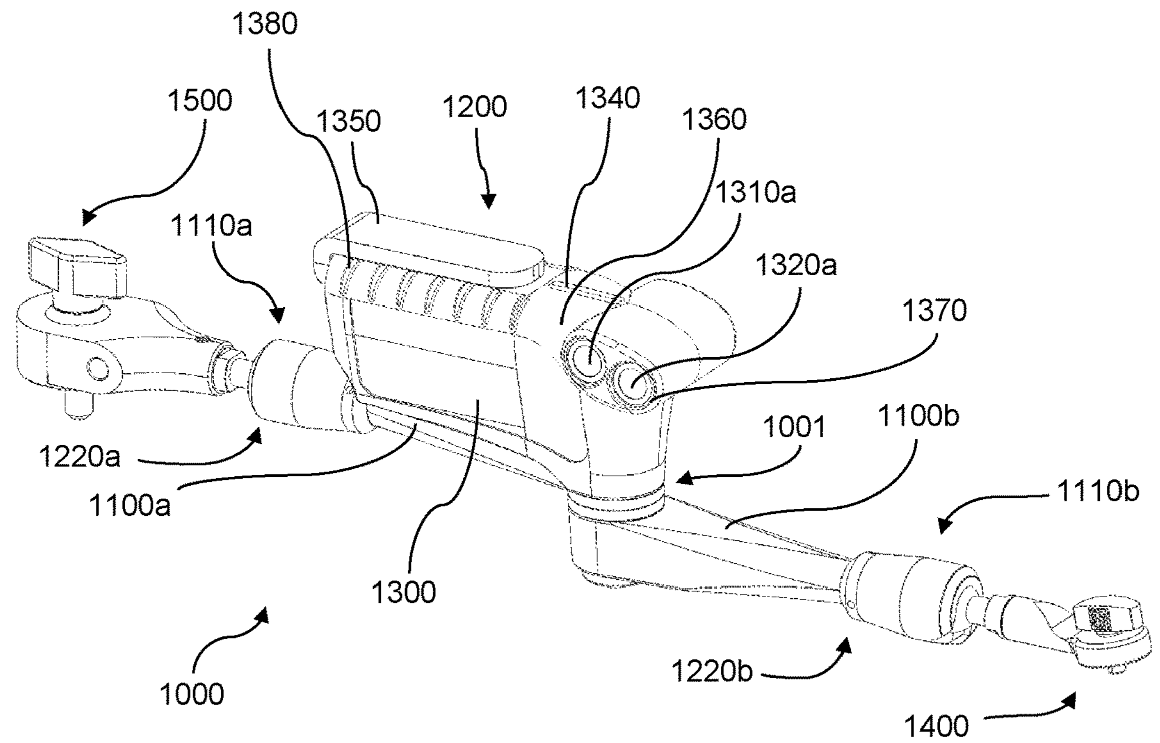
FIG. 1 depicts an illustration of a motorized positioning arm according to the invention with closed housing.

FIG. 1 shows an illustration of a motorized positioning arm 1000 according to the invention. The motorized positioning arm 1000 comprises two arm elements **1100*a*, 1100*b*. The two arm elements 1100*a* and 1100*b* are pivotally connected to each other by means of a central joint 1001**.

The arm element **1100*a* comprises two ends. One end is connected with the central joint 1001 and the other end 1120*a* is connected with a further joint 1110*a*. The further joint 1110*a* is configured as a ball joint. The further joint 1110*a* is connected with a fastening device 1500. Here, the fastening device 1500 is illustrated, for example, as a screwable connection. The fastening device 1500** can be connected, for example, with an operating table.

The arm element **1100*b* also comprises two ends. Here, one end is connected with the central joint 1001 and the other end 1120*b* is connected with a further joint 1110*b*. The further joint 1110*b* is also configured as a ball joint. The further joint 1110*b* is connected with an instrument holder 1400. For example, a medical instrument can be arranged on the instrument holder 1400. Even if the instrument holder 1400 is illustrated with a screw connection, the instrument holder 1400 is preferably configured as a clamping connection. In this way, a suitable clamping piece on the medical instrument can be clamped into the instrument holder from the outside without violating a sterile drape enveloping the motorized positioning arm 1000**.

All joints 1001, **1110*a*, 1110*b* are lockable and releasable by means of a common blocking mechanism 1200. The blocking mechanism 1200 is not visible in FIG. 1 because it is arranged within a housing 1300**.

The housing 1300 comprises a cover element 1360. The cover element 1360 may be made of plastic, for example. The rest of the housing 1300 may be configured integrally with the arm element **1100*a*, as illustrated in FIG. 1. Thus, the rest of the housing 1300 may be configured from the material of the arm element 1100*a***, for example aluminium.

Operating elements **1310*a*, 1320*a* for operating the blocking mechanism 1200 are arranged on the housing 1300. In a combination of FIG. 1 and FIG. 5, it can be seen that the operating elements 1310*a* and 1320*a* each comprise redundant operating elements 1310*b*, 1320*b* on the opposite side. This enables particularly safe operation. Here, the operating elements 1310***a* and 1310*b*, and the operating elements 1320*a* and 1320*b* belong together, i.e., must be operated together. Here, the operating elements 1310*a*, 1310*b*, 1320*a*, 1320*b* are configured as buttons which are arranged within a pocket 1370 in the housing 1300, more precisely in the cover element 1360 thereof. Because of the pocket 1370, the operating elements 1310*a*, 1310*b*, 1320*a*, 1320*b* are on the one hand well tactilely perceptible and on the other hand protected from unintentional operation.

The entire housing 1300 is ergonomically configured as a handle. Thus, a user can grip the handle-shaped housing 1300, wherein, for example, thumb and index finger or thumb and middle finger can simultaneously operate the operating elements 1320*a*, 1320*b* or 1310*a*, 1310*b*. For example, actuation of the operating elements 1310*a*, 1310*b* may result in blocking of the joints 1001, 1110*a*, 1110*b* and actuation of the operating elements 1320*a*, 1320*b* may result in releasing of the joints 1001, 1110*a*, 1110*b*, or vice versa. The rest of the hand can then grip or hold the housing 1300 and position the arm element 1100*a*. In doing so, the palm of the hand rests on the housing 1300. The housing 1300 may comprise a structure 1380 that assists in gripping the housing 1300. Alternatively, or additionally, the housing 1300 may be coated with an anti-slip coating.

The housing 1300 comprises at least one indicator element 1340 configured, for example, to indicate a state of the blocking mechanism 1200. In FIG. 1, the indicator element 1340 is configured as a visual indicator, more specifically an LED.

Figure 2:
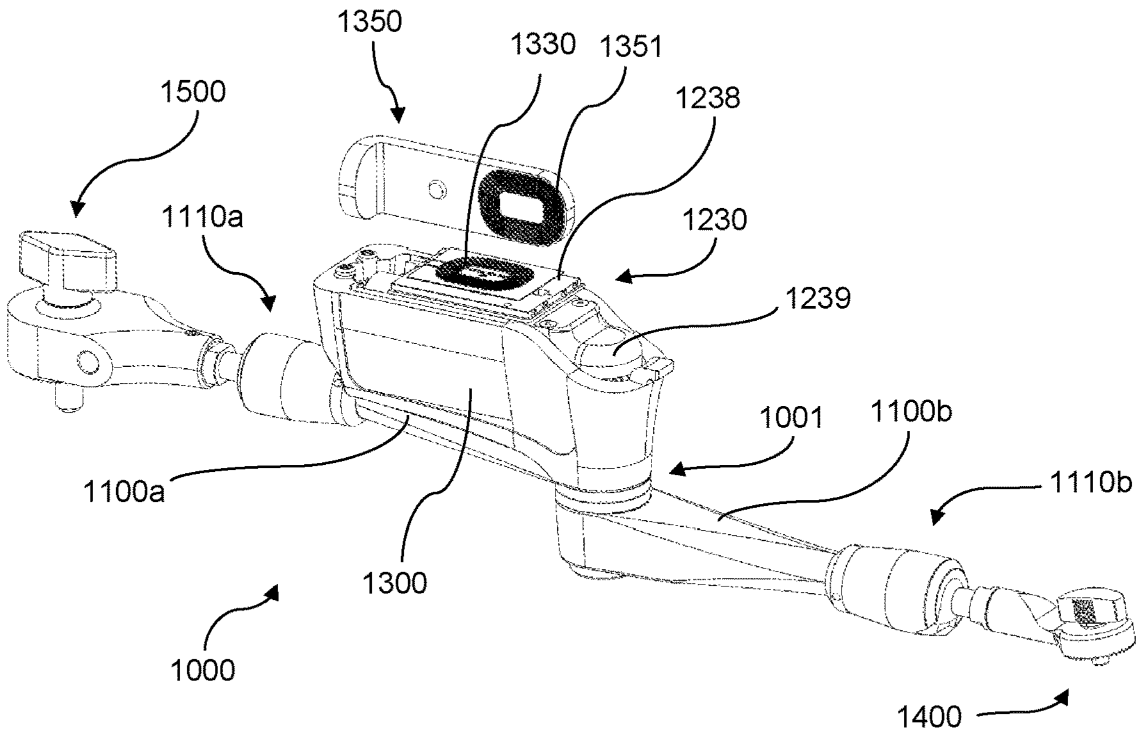
FIG. 2 depicts the motorized positioning arm shown in FIG. 1 without cover element and with the charging device lifted off.

FIG. 2 shows the motorized positioning arm 1000 shown in FIG. 1 without the cover element 1360. Most of the components shown in FIG. 2 have already been described with reference to FIG. 1. Most of the aspects already known will not be described again below. However, all aspects or components already described with respect to FIG. 1 are transferable to FIG. 2 and the following figures.

Since the cover element 1360 is not illustrated in FIG. 2, first components of an electrical blocking device 1230 belonging to the blocking mechanism 1200 can be seen, which are accommodated in the housing 1300.

In particular, an accumulator 1238 can be seen which serves to drive the electrical blocking device 1230. The accumulator 1238 is inductively chargeable by means of a charging coil 1330. The charging coil 1330 is arranged at least substantially directly below the cover element 1360.

For charging the accumulator 1238, the motorized positioning arm 1000 comprises a charging device 1350. The charging device 1350 is shown in FIG. 1 in a position charging the accumulator 1238, in which the charging device 1350 is arranged at a predefined position on the housing 1300, more specifically the cover element 1360 thereof. In the case of the charging device 1350 shown in FIG. 2, which is raised and rotated 90°, the charging coil 1351 corresponding to the charging coil 1330 is shown.

The indicator element 1340 may be configured, for example, to indicate a charging state of the accumulator 1238 and/or a blocking state of the blocking mechanism 1200.

FIG. 2 further shows a cover 1239 of the electrical blocking device 1230 of the blocking mechanism 1200.

Figure 3:
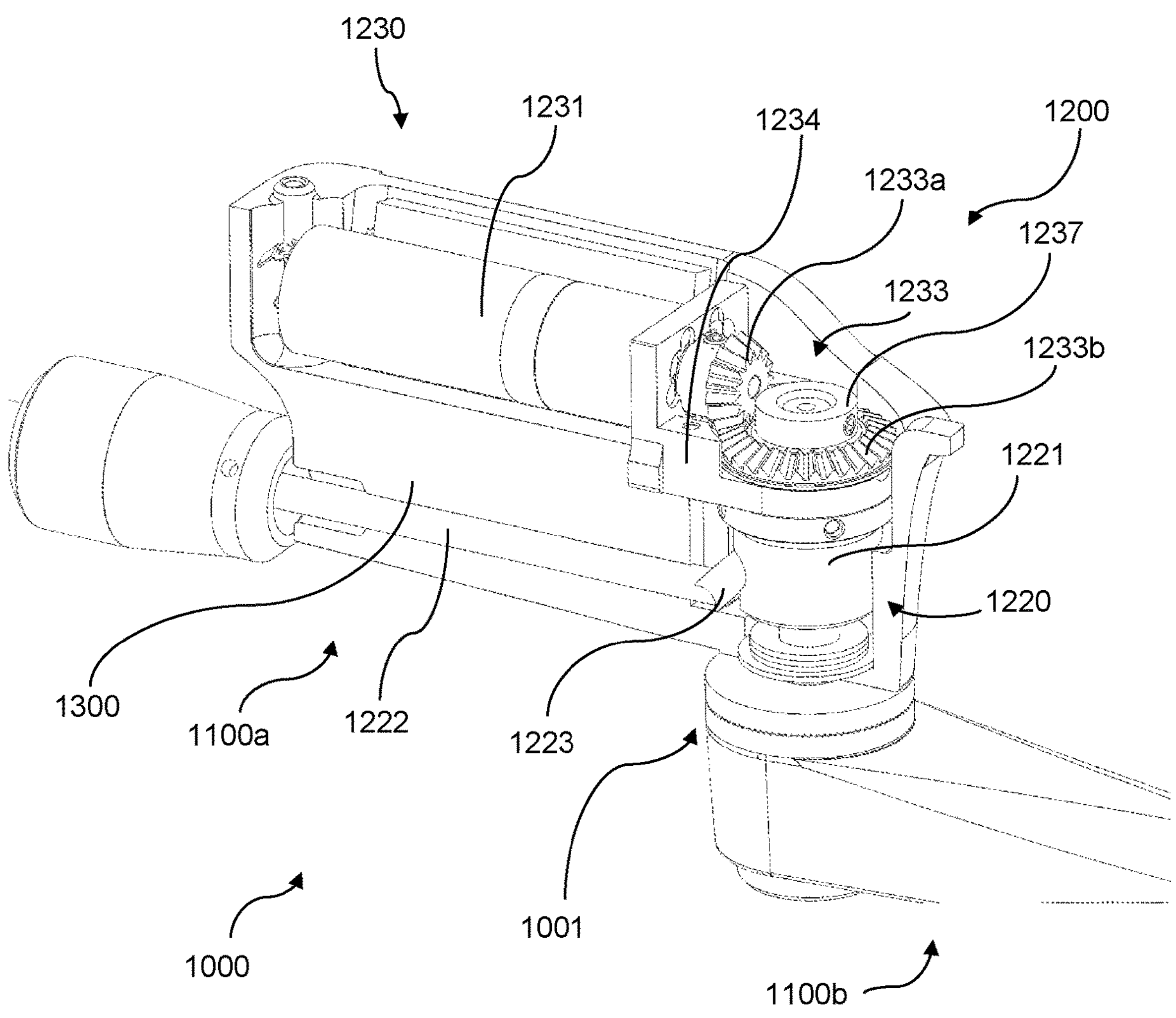
FIG. 3 depicts a more detailed illustration of the motorized positioning arm according to the invention with a partially hidden housing and a visible electrical blocking device according to the invention.

FIG. 3 shows a slightly more detailed illustration of the motorized positioning arm 1000 according to the invention, in which the housing 1300 is half hidden to show the blocking mechanism 1200 in more detail.

In addition to the electrical blocking device 1230, the blocking mechanism 1200 comprises a transmission device 1220 configured to transmit a blocking motion or release motion to the further joints 1110*a* and 1110*b*. For simplicity, the transmission device 1220 is illustrated in FIG. 3 for the arm element 1100*a* only.

The transmission device 1220 comprises a clamping sleeve 1221 that can transmit motion to a push rod 1222 by means of a cam 1223. In more detail, in FIG. 3, the push rod 1222 moves to the left when the clamping sleeve 1221 moves downward. By moving the push rod 1222 to the left, the further joint 1110*a* is blocked.

The electrical blocking device 1230 comprises an electric motor 1231. As can be seen in FIG. 3, the electric motor 1231 is oriented and arranged at least substantially parallel to the axial direction of the arm element 1100*a*. Thus, the electric motor 1231 can be arranged on the arm element 1100*a* in a particularly space-saving manner. However, such an arrangement of the electric motor 1231 requires the output movement of the electric motor 1231 to be converted. For this purpose, the electrical blocking device 1230 comprises a bevel gearing 1233.

For example, the bevel gearing 1233 is not visible in FIG. 2 because it is covered by the cover 1239. The cover 1239 serves to protect the bevel gearing 1233. In FIG. 3, however, the cover 1239 is not shown for better visibility of the mechanism.

The bevel gearing 1233 comprises an input gear 1233*a* formed as a bevel gear and an output gear 1233*b* formed as a bevel gear. The output gear 1233*b* is larger than the input gear 1233*a*, so that a transmission to slow occurs, i.e. a reduction gear is provided. The shafts on which the input gear 1233*a* and the output gear 1233*b* are arranged are perpendicular to each other.

Figure 4:
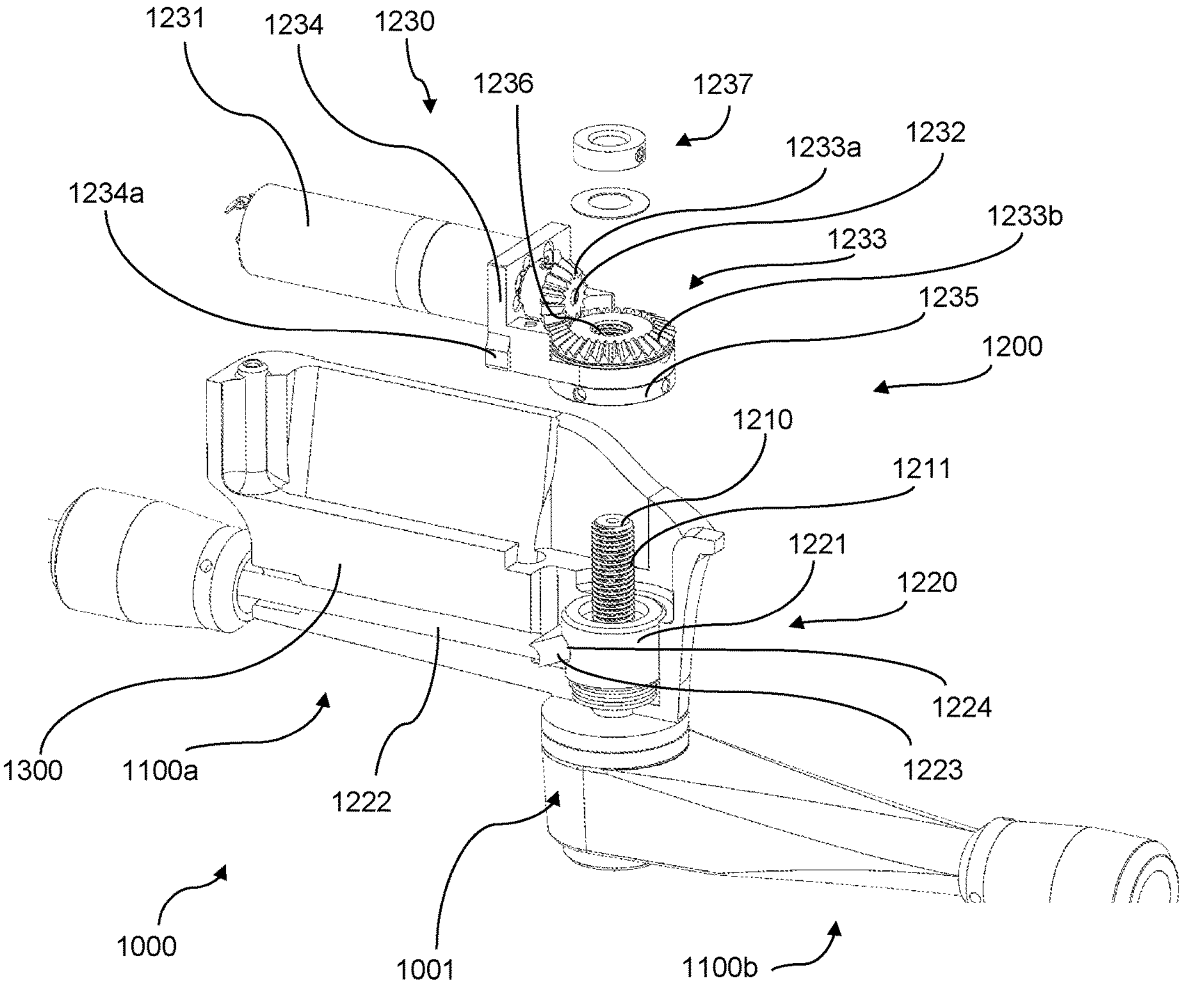
FIG. 4 depicts a more detailed illustration of the motorized positioning arm according to the invention with a partially hidden housing and an electrical blocking device according to the invention detached from a central shaft.

This is better seen in FIG. 4, which shows a more detailed illustration of the motorized positioning arm 1000 according to the invention with a partially hidden housing 1300 and an electrical blocking device 1230 spaced from the rest of the motorized positioning arm 1000. In FIG. 4, the electrical blocking device 1230 is shown detached from a central shaft 1210. The central shaft 1210 is operatively connected with the output gear 1233*b*. For this purpose, the central shaft 1210 comprises an external thread 1211 and the output gear 1233*b* comprises an internal thread 1236. As can be seen in FIG. 4, the electric motor 1231 comprises an output shaft 1232, which is the shaft arranged perpendicular to the central shaft 1210 to which the input gear 1233*a* is attached.

As can be seen in FIG. 3 and FIG. 4, the electrical blocking device 1230 comprises an angled piece 1234 that supports the bevel gearing 1233. The angled piece 1234 is further configured to prevent the electrical blocking device 1230 from being rotated during operation. As shown in FIG. 4, the angled piece 1234 comprises a stop 1234*a* for this purpose. The stop 1234*a* comes into contact with the housing 1300 and thus prevents the electrical blocking device 1230 from being rotated.

Figure 5:
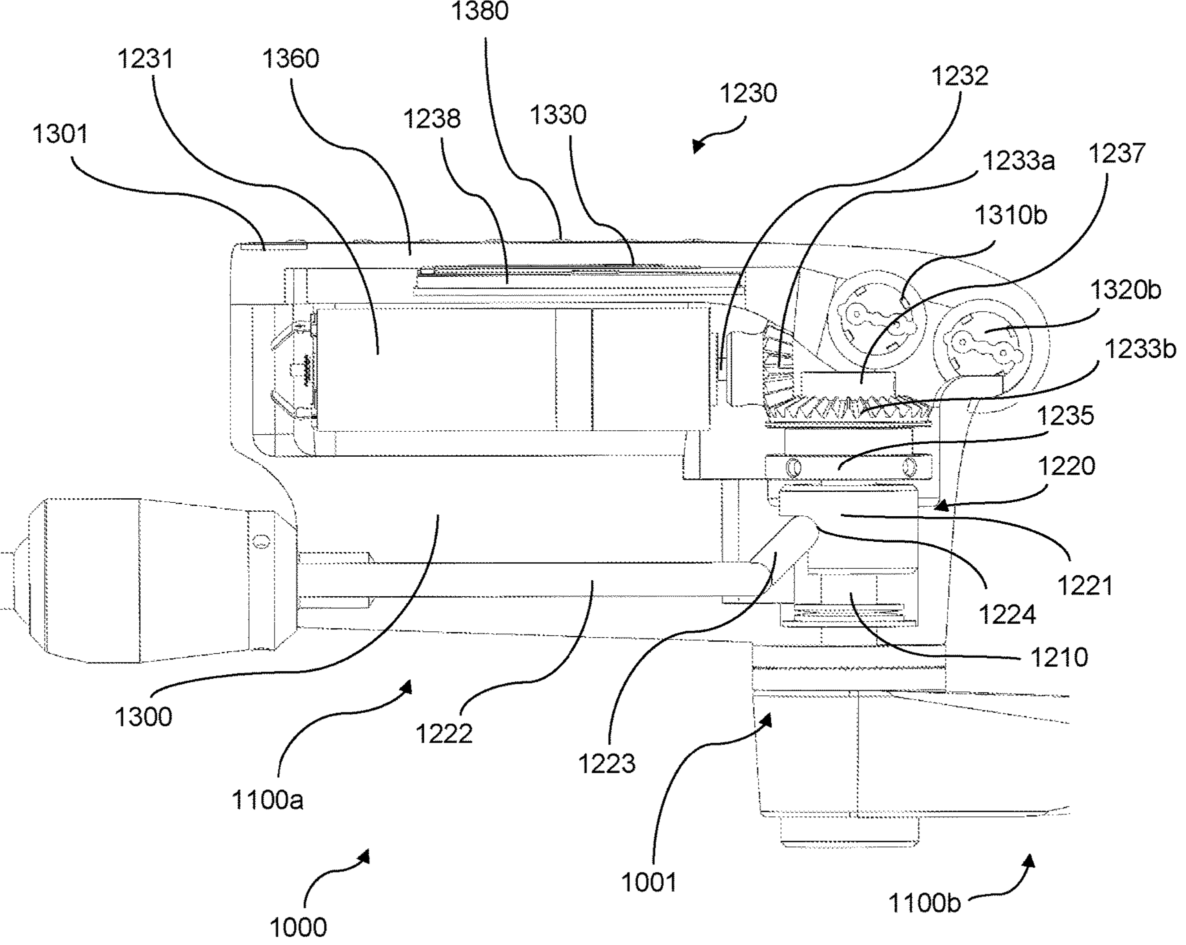
FIG. 5 depicts a simplified sectional view of the motorized positioning arm according to the invention.

In operation, when the electrical blocking device 1230 is arranged on the central shaft 1210 as shown in FIG. 3 or FIG. 5, the electrical blocking device 1230 moves downward or upward along the central shaft 1210. Therefore, the electrical blocking device 1230 is floatingly, i.e. movably, arranged within the housing 1300. For example, movement of the electrical blocking device 1230 may be guided only by means of the central shaft 1210 and laterally by the housing 1300 and the stop 1234*a*, which prevent rotation. However, a linear guide may alternatively be arranged in the housing 1300.

When the electrical blocking device 1230 is moved downward in the axial direction of the central shaft 1210, that is, in the direction of the arm elements 1100*a* and 1100*b*, the joints 1001, 1110*a* and 1110*b* are blocked. The blocking of the joints 1001, 1110*a* and 1110*b* do not have to occur simultaneously. Rather, it is preferred that joints 1001, 1110*a*, and 1110*b* block progressively. If the joints 1001, 1110*a* and 1110*b* can be progressively or sequentially blocked or released, the degrees of freedom of movement of the motorized positioning arm 1000 are also only progressively limited and released. Thus, on the one hand, an easier adjustment of the position of the motorized positioning arm 1000 and, on the other hand, a certain stabilization during release can be achieved. For example, the further joint 1110*a* may be blocked first, then the central joint 1001, and then the further joint 1110*b*.

The order in which the joints 1001, 1110*a* and 1110*b* block may be affected by adjusting the components of the transmission device 1200. Adjustment can be made for the arm element 1100*a* by varying the lengths of the clamping sleeve 1221 and the push rod 1222. The same applies to the arm element 1100*b*, where the lengths of the associated clamping sleeve and push rod can also be varied. If, for example, the clamping sleeve 1221 is shortened, the clamping of the central joint 1001 is affected later than that of the further joint 1110*a*.

During blocking, the electrical blocking device 1230, which moves downward due to the functional connection between the internal thread 1236 and the external thread 1211 as seen in FIG. 5, also presses the clamping sleeve 1221 downward. As a result, the cam 1223 arranged in a joint socket 1224 on the clamping sleeve 1221 moves downward with it and pushes the push rod 1222 to the left, i.e., in the direction of the further joint 1110*a*. This causes the further joint 1110*a* to be blocked. The transmission device of the other arm element 1100*b* is not illustrated. However, this transmission device can also be configured by means of a clamping sleeve and push rod. The transmission device or the part of the transmission device of the other arm element 1100*b* is similarly constructed. However, for example, a clamping sleeve of the other arm element 1100*b* may comprise an internal thread so that the clamping sleeve may move upward (blocking movement) or downward (releasing movement) when the electrical blocking device 1230 is being blocked.

When releasing, the electrical blocking device 1230 moves upward on the central shaft 1210. To limit the upward movement of the electrical blocking device 1230, the electrical blocking device 1230 comprises a stopper 1237. As can be readily seen, particularly in FIG. 4, the stopper 1237 is configured in an annular shape and is arranged on an upper end of the central shaft 1210.

To allow movement of the electrical blocking device 1230, the output gear 1233*b* is supported by means of dry bearings 1235. As can also be seen particularly in FIG. 4, the dry bearings 1235 are configured to be at least substantially annular. For example, these are configured as slide promotion plastic rings.

As can be seen in FIG. 5, the housing 1300 comprises a centering 1301. This centering 1301 serves to enable reliable arrangement of the charging device 1350 (see FIG. 1).

Some advantageous embodiments of the device according to the invention have been described above. The invention is however not limited to the embodiments described above, as the inventive idea can be applied in numerous ways within the scope of the claims.

The invention claimed is:

1. A motorized positioning arm for at least one of positioning instruments and, medical instruments, the motorized positioning arm comprising:

at least two arm elements connected to one another so as to be pivotable about a pivot axis by a central joint, wherein at least one of the at least two arm elements comprises a further joint at an end opposite to the central joint, wherein the motorized positioning arm further comprises a blocking mechanism configured to block and release the central joint and the at least one further joint, wherein the blocking mechanism further comprises a central shaft arranged coaxially with the pivot axis, and at least one transmission device from the central shaft to the at least one further joint, wherein the blocking mechanism further comprises an electrical blocking device in engagement with the central shaft so as to enable blocking and unblocking of the joints, and wherein the electrical blocking device is configured and arranged to move relative to and along the central shaft, thereby blocking or unblocking the joints.

2. The motorized positioning arm according to claim 1, wherein the further joint comprises a first further joint and a second further joint, wherein each of the at least two arm elements comprise one of the first and second further joints respectively at the end opposite the central joint, and wherein the at least one transmission device comprises a first transmission device and a second transmission device, wherein the blocking mechanism comprises the first and second transmission devices to each of the first and second further joints, respectively.

3. The motorized positioning arm according to claim 1, wherein the further joint is configured as a ball joint.

4. The motorized positioning arm according to claim 1, wherein: the electrical blocking device comprises an electric motor with an output shaft, and the output shaft is arranged perpendicular to the central shaft.

5. The motorized positioning arm according to claim 4, wherein the electrical blocking device comprises: a bevel gearing with an input gear connected to the output shaft of the electric motor; and an output gear engaged with the central shaft.

6. The motorized positioning arm according to claim 5, wherein the output gear is configured and arranged to be supported by an at least substantially annular dry bearing.

7. The motorized positioning arm according to claim 5, wherein the output gear comprises an internal thread and the central shaft comprises an external thread complementary to the internal thread.

8. The motorized positioning arm according to claim 7, wherein the electrical blocking device is arranged on one of the at least two arm elements and the output shaft of the electric motor extends at least substantially parallel to the axial direction of the arm element on which the electrical blocking device is arranged.

9. The motorized positioning arm according to claim 8, wherein the electrical blocking device is releasably arranged on the arm element on which the electrical blocking device is arranged.

10. The motorized positioning arm according to claim 8, wherein the electrical blocking device is a movable clamping unit, which configured to be movable in an axial direction of the central shaft relative to the arm element on which the electrical blocking device is arranged.

11. The motorized positioning arm according to claim 1, wherein: the motorized positioning arm comprises a housing configured to at least substantially enclose the electrical blocking device, and the housing is configured in a shape of a handle.

12. The motorized positioning arm according to claim 11, wherein the electrical blocking device comprises a stop configured and arranged to come into abutment with the housing thereby preventing the electrical blocking device from rotating with the housing when blocking and releasing the joints.

13. The motorized positioning arm according to claim 11, wherein redundant operating elements are arranged on the housing for controlling the electric motor.

14. The motorized positioning arm according to claim 11, further comprising a charging coil arranged within the housing, the charging coil configured to wirelessly charge an accumulator configured to drive the electric motor.

15. The motorized positioning arm according to claim 11, further comprising at least one indicator element arranged on the housing, the at least one indicator element configured to indicate at least one of a charging state of the accumulator and a blocking state of the blocking mechanism.

* * * * *